US00PP21482P2

(12) United States Plant Patent
Pieters

(10) Patent No.: US PP21,482 P2
(45) Date of Patent: Nov. 16, 2010

(54) ***CHRYSANTHEMUM* PLANT NAMED 'PPP REML 09'**

(50) Latin Name: *Chrysanthemum morifolium*
Varietal Denomination: PPP REML 09

(75) Inventor: Dirk Pieters, Oostnieuwkerke (BE)

(73) Assignee: Paraty BYBA, Oostnieuwkerke (BE)

( * ) Notice: Subject to any disclaimer, the term of this patent is extended or adjusted under 35 U.S.C. 154(b) by 0 days.

(21) Appl. No.: 12/462,529

(22) Filed: Aug. 5, 2009

(51) Int. Cl.
*A01H 5/00* (2006.01)

(52) U.S. Cl. ..... Plt./287

(58) Field of Classification Search ..... Plt./287
See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by decorative type inflorescences, consistent flowering response to short days, blooming consistently after 49 days of short day length, lilac-colored ray florets, free branching habit, and a consistent natural season flowering habit during the third week of September.

1 Drawing Sheet

Latin name of the genus and species: *Chrysanthemum morifolium.*

Variety denomination: 'PPP REML 09'.

BACKGROUND OF THE INVENTION

The new cultivar 'PPP REML 09' is a product of a cross between the male parent 'GEDI ONE JAM' (U.S. Plant Pat. No. 13,891) and the female parent 'GEDI ONE CAR' (U.S. Plant Pat. No. 13,794). The new cultivar was discovered and selected by Dirk Pieters in October of 1997 in a greenhouse in Oostnieuwkerke, Belgium.

Asexual reproduction of the new cultivar 'PPP REML 09' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP REML 09' has not been observed under all possible environmental conditions. The phenotype may vary somewhat with variations in environment such as temperature, daylength, and light intensity, without, however, any variance in genotype. The following traits have been repeatedly observed and are determined to be the unique characteristics of 'PPP REML 09.' These characteristics in combination distinguish 'PPP REML 09' as a new and distinct *Chrysanthemum* cultivar:

1. Decorative-type, lilac-colored inflorescences;
2. Consistent natural season flowering habit during the third week of September;
3. Free branching habit; and
4. Consistent flowering response to short days, blooming consistently after 49 days of short day length.

Plants of the new cultivar 'PPP REML 09' are similar to plants of the male parent variety, 'GEDI ONE JAM' in most horticultural characteristics; however plants of the new cultivar 'PPP REML 09' are shorter. Also, the new cultivar 'PPP REML 09' has a smaller inflorescence diameter and longer inflorescence longevity. Additionally, the male parent 'GEDI ONE JAM' has more inflorescences per lateral branch. Finally, the ray florets of 'PPP REML 09' are a much darker purple than the ray florets of the male parent 'GEDI ONE JAM'.

Plants of the new cultivar 'PPP REML 09' are similar to plants of the female parent variety, 'GEM ONE CAR' in most horticultural characteristics, however plants of the new cultivar 'PPP REML 09' are shorter but have a wider plant spread. Also, the new cultivar 'PPP REML 09' has a larger inflorescence diameter and longer inflorescence longevity. Finally, 'PPP REML 09' naturally blooms one to two weeks earlier than the female parent 'GEM ONE CAR'.

In comparison to the commercially available variety 'GEDI TWO CAN' (U.S. Plant Pat. No. 14,474), 'PPP REML 09' is taller and wider. Additionally, the new variety 'PPP REML 09' has a larger inflorescence diameter and darker purple ray florets. Further, the new variety 'PPP REML 09' has more ray florets per inflorescence. Finally, 'PPP REML 09' has longer inflorescence longevity.

BRIEF DESCRIPTION OF THE PHOTOGRAPH

The accompanying photograph in the drawing illustrates in full color a typical plant of 'PPP REML 09' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP REML 09' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP REML 09'.
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 24 cm.
Plant spread: Approximately 36 cm.
Growth rate: Moderate.
Branching characteristics: Free Branching.
Length of lateral branches: Approximately 19 cm.
Number of leaves per lateral branch: Approximately 28.
Age of plant described: Approximately 145 days.

FOLIAGE

Leaf:
*Arrangement.*—Alternate single.
*Average length.*—Approximately 4.5 cm.
*Average width.*—Approximately 3.1 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 0.6 cm.
*Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.
*Venation.*—Type: Palmately net. Venation color upper side: Near Green 138A. Venation color under side: Near Green 138B.

Petiole:
*Average length.*—Approximately 1 cm.
*Color.*—Near Green 138B.
*Diameter.*—Approximately 0.1 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the third week in September.
*Number of inflorescences per lateral branch.*—Approximately 6.
*Inflorescence diameter.*—Approximately 6.2 cm.
*Inflorescence depth.*—Approximately 2.3 cm.
*Inflorescence longevity on plant.*—Approximately 28 to 34 days.
*Persistence.*—Persistent.
*Receptacle height.*—5 mm.
*Receptacle diameter.*—5 mm.
*Fragrance.*—None.

Ray Florets:
*Appearance.*—Matte.
*Texture* (*upper and lower*).—Smooth.
*Average number of ray florets per inflorescence.*—188.
*Shape.*—Spoon.
*Aspect.*—Flat.
*Margin.*—Entire.
*Apex.*—Obtuse.
*Length.*—Approximately 2.5 cm.
*Width.*—Approximately 0.4 cm.
*Color.*—Upper surface at first opening: Near Red-Purple 64A. Upper surface at maturity: Near Purple 77A. Upper surface at fading: Near Purple 77C. Under surface at first opening: Near Red-Purple 64A. Under surface at maturity: Near Purple 77C. Under surface at fading: Near Purple 77D.

Disc florets:
*Appearance.*—Shiny.
*Texture.*—Smooth.
*Average number of florets per disc.*—Approximately 2.
*Shape.*—Cylindric.
*Apex.*—Obtuse.
*Average length.*—Approximately 0.4 cm.
*Average width.*—Approximately 0.1 cm.
*Color.*—At first opening: Near Yellow-Green 154B. At maturity: Near Yellow 13B. At fading: Near Yellow 13B.

Peduncle:
*Length.*—At terminal end (shortest): Approximately 3 cm. At lateral end (longest): Approximately 8 cm.
*Angle to stem.*—Acute.
*Strength.*—Moderate.
*Color.*—Near Greyed-Green 189A.
*Habit.*—Upright.
*Diameter.*—Approximately 0.2 cm.
*Surface texture.*—Lightly pubescent.

Inflorescence bud:
*Length.*—Approximately 0.5 cm.
*Diameter.*—Approximately 0.6 cm.
*Form.*—Globular.
*Color.*—Near Red-Purple 64A.

Involucral bracts (phyllaries):
*Appearance.*—Matte.
*Texture.*—Lightly pubescent.
*Number.*—Approximately 100.
*Shape.*—Lanceolate.
*Margin.*—Entire.
*Apex.*—Obtuse.
*Length.*—Approximately 0.5 cm.
*Width.*—Approximately 0.2 cm.
*Color.*—Upper side: Near Green 137A. Under side: Near Green 137B.

REPRODUCTIVE ORGANS

Ray florets: Number of pistils per floret: 1. Stigma shape: 2 branched. Stigma color: Near Yellow 9A. Style color: Near green-Yellow 1D. Style length: Approximately 0.3 cm. Stamens: Absent.

Disc florets: Number of pistils per floret: 1. Stigma shape: Cylindric. Stigma color: Near Yellow 13A. Style length: Approximately 0.2 cm. Style color: Near Green-Yellow 1D. Number of stamens per floret: Approximately 5.

Anther shape: Tubular. Anther color: Near Yellow 13A. Pollen color: No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP REML 09' as herein illustrated and described.

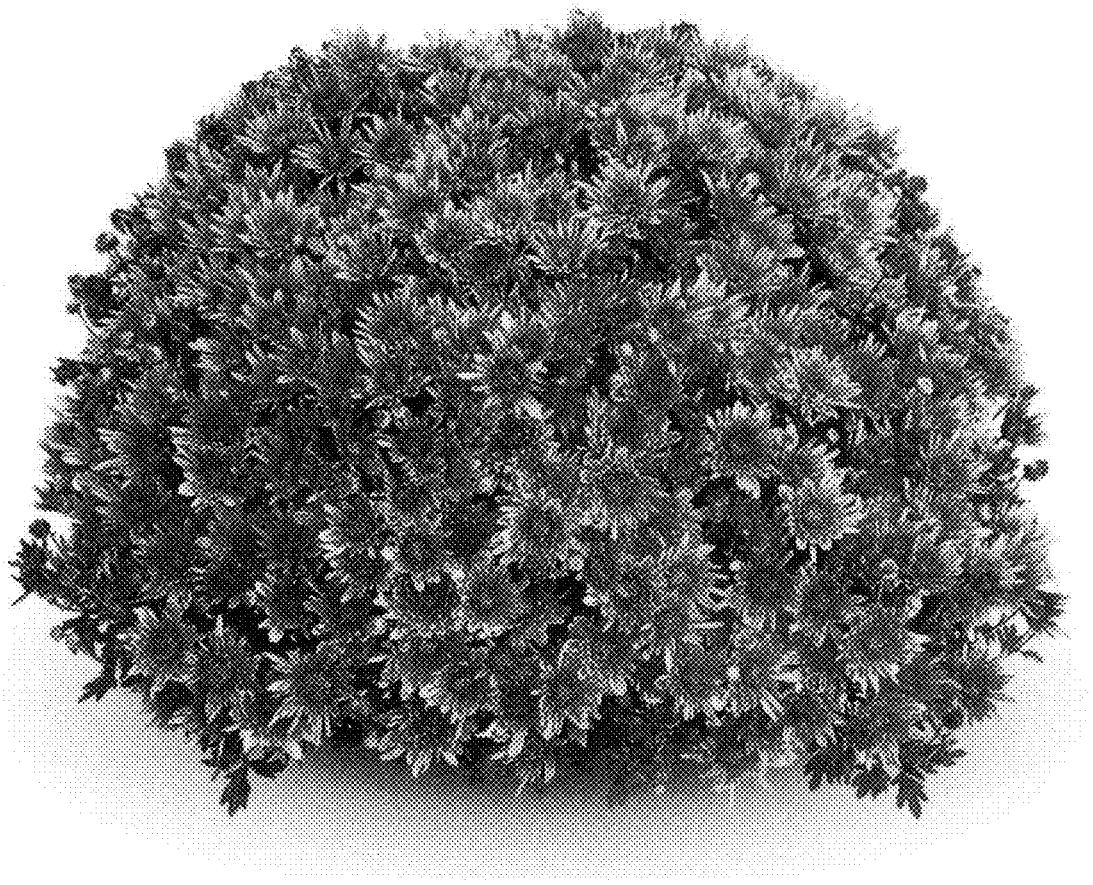

* * * * *